(12) United States Patent
Khan et al.

(10) Patent No.: US 8,293,805 B2
(45) Date of Patent: Oct. 23, 2012

(54) TRACKING FEEDSTOCK PRODUCTION WITH MICRO SCALE GAS-TO-LIQUID UNITS

(75) Inventors: Moinuddin Khan, Houston, TX (US); Andrew Kurkjian, Sugar Land, TX (US); Stephen C. Leviness, Tulsa, OK (US); Keith Massie, Aberdeen (GB); John Nighswander, Houston, TX (US)

(73) Assignee: Schlumberger Technology Corporation, Sugar Land, TX (US)

( * ) Notice: Subject to any disclaimer, the term of this patent is extended or adjusted under 35 U.S.C. 154(b) by 1152 days.

(21) Appl. No.: 12/129,401

(22) Filed: May 29, 2008

(65) Prior Publication Data

US 2009/0299795 A1    Dec. 3, 2009

(51) Int. Cl.
*C07C 27/06* (2006.01)
(52) U.S. Cl. .................................................. 518/702
(58) Field of Classification Search .................. None
See application file for complete search history.

(56) References Cited

U.S. PATENT DOCUMENTS

| | | | |
|---|---|---|---|
| 3,050,456 A | 10/1957 | Melchior | |
| 4,048,250 A | 9/1977 | Garwood et al. | |
| 4,207,208 A | 6/1980 | Lucki et al. | |
| 4,525,206 A | 6/1985 | Soled et al. | |
| 4,607,020 A | 8/1986 | Soled et al. | |
| 4,663,305 A | 5/1987 | Mauldin et al. | |
| 4,670,414 A | 6/1987 | Kobylinski et al. | |
| 4,670,475 A | 6/1987 | Mauldin | |
| 4,717,702 A | 1/1988 | Beuther et al. | |
| 4,729,981 A | 3/1988 | Kobylinski et al. | |
| 4,738,948 A | 4/1988 | Iglesia et al. | |
| 4,769,127 A | 9/1988 | Erickson et al. | |
| 4,801,573 A | 1/1989 | Eri et al. | |
| 4,822,824 A | 4/1989 | Iglesia et al. | |
| 4,827,152 A | 5/1989 | Farkas | |
| 4,857,497 A | 8/1989 | De Jong et al. | |
| 4,863,894 A | 9/1989 | Chinchen et al. | |
| 4,962,078 A | 10/1990 | Behrmann et al. | |
| 4,967,096 A | 10/1990 | Diemer et al. | |
| 5,128,377 A | 7/1992 | Behrmann et al. | |
| 5,169,869 A | 12/1992 | Miller et al. | |
| 5,260,239 A | 11/1993 | Hsia | |
| 5,283,216 A | 2/1994 | Mitchell | |
| 5,288,673 A | 2/1994 | Behrmann et al. | |
| 5,389,690 A | 2/1995 | Mitchell | |
| 5,581,128 A | 12/1996 | Royle | |
| 5,585,316 A | 12/1996 | Nay et al. | |
| 5,628,344 A | 5/1997 | Roberts | |
| 5,756,419 A | 5/1998 | Chaumette et al. | |
| 5,817,701 A | 10/1998 | Leviness et al. | |
| 5,844,005 A | 12/1998 | Bauman et al. | |
| 5,928,985 A | 7/1999 | Williams | |
| 6,005,011 A | 12/1999 | Henningsen | |
| 6,022,755 A | 2/2000 | Kinnari et al. | |
| 6,162,754 A | 12/2000 | Maretto et al. | |
| 6,185,388 B1 | 2/2001 | Yamamoto | |
| 6,188,139 B1 | 2/2001 | Thaxton et al. | |
| 6,201,030 B1 | 3/2001 | Beer | |
| 6,225,359 B1 | 5/2001 | O'Rear et al. | |
| 6,296,686 B1 | 10/2001 | Prasad et al. | |
| 6,300,268 B1 | 10/2001 | Lapidus et al. | |
| 6,444,712 B1 | 9/2002 | Janda | |
| 6,455,596 B2 | 9/2002 | Lapidus et al. | |
| 6,455,623 B1 | 9/2002 | Howard | |
| 6,475,375 B1 | 11/2002 | Dancuart | |
| 6,486,220 B1 | 11/2002 | Wright | |
| 6,537,945 B2 | 3/2003 | Singleton et al. | |
| 6,706,661 B1 | 3/2004 | Krylova et al. | |
| 6,716,886 B2 | 4/2004 | Krylova et al. | |
| 6,753,286 B2 | 6/2004 | Clark et al. | |
| 6,753,351 B2 | 6/2004 | Clark et al. | |
| 6,753,354 B2 | 6/2004 | Koveal et al. | |
| 6,777,451 B2 | 8/2004 | Koveal et al. | |
| 6,800,579 B2 | 10/2004 | Daage et al. | |
| 6,812,179 B2 | 11/2004 | Huang et al. | |
| 6,838,487 B1 | 1/2005 | Demirel et al. | |
| 6,869,978 B2 | 3/2005 | Wright et al. | |
| 6,871,504 B2 | 3/2005 | Kuroki et al. | |
| 6,878,655 B2 | 4/2005 | Raje et al. | |
| 6,900,151 B2 | 5/2005 | Soled et al. | |
| 6,949,488 B2 | 9/2005 | Belt et al. | |
| 6,962,947 B2 | 11/2005 | Wright et al. | |
| 6,989,403 B2 | 1/2006 | Huang et al. | |
| 7,018,450 B2 | 3/2006 | Rojey et al. | |
| 7,067,561 B2 | 6/2006 | Bowe | |
| 7,102,331 B2 | 9/2006 | Walter et al. | |
| 7,108,070 B2 | 9/2006 | Hall et al. | |
| 7,303,731 B2 | 12/2007 | Demirel et al. | |
| 7,629,701 B2 | 12/2009 | Campanile et al. | |
| 7,669,418 B2 | 3/2010 | Chino et al. | |
| 2003/0121200 A1 | 7/2003 | Iijima et al. | |
| 2003/0225169 A1 | 12/2003 | Yetman | |
| 2004/0123518 A1 | 7/2004 | Eastman et al. | |
| 2004/0180972 A1 | 9/2004 | Ansorge et al. | |
| 2004/0211316 A1 | 10/2004 | Collins | |
| 2004/0242941 A1 | 12/2004 | Green et al. | |
| 2005/0106086 A1 | 5/2005 | Tomlinson et al. | |
| 2005/0222278 A1* | 10/2005 | Agee et al. ................... 518/702 |
| 2005/0232857 A1 | 10/2005 | Lomax, Jr. et al. | |
| 2007/0004810 A1 | 1/2007 | Wang et al. | |
| 2007/0112080 A1 | 5/2007 | Green et al. | |
| 2007/0208090 A1* | 9/2007 | van Dijk ....................... 518/702 |
| 2008/0245071 A1 | 10/2008 | Kawakami et al. | |
| 2008/0262110 A1 | 10/2008 | Lomax et al. | |
| 2009/0221723 A1 | 9/2009 | Leviness et al. | |
| 2010/0000153 A1 | 1/2010 | Kurkjian et al. | |

FOREIGN PATENT DOCUMENTS

| | | |
|---|---|---|
| GB | 2380739 A | 4/2003 |
| WO | 03099961 A2 | 12/2003 |
| WO | WO2004/011574 | 2/2004 |
| WO | WO2006/012116 | 2/2006 |
| WO | 2006058107 A1 | 6/2006 |
| WO | 2007127898 A2 | 11/2007 |

* cited by examiner

*Primary Examiner* — Sudhakar Katakam

(57) ABSTRACT

A method of tracking production from an NG source that includes the steps of providing one or more micro-scale GTL units, feeding NG from the source to the micro-scale GTL units, operating the micro-scale GTL units and adjusting the number of micro-scale GTL units employed to track or match the production from the source is provided. In some aspects of the invention, the micro-scale GTL unit includes both syngas manufacture and liquid product synthesis. The liquid product synthesis step may produce methanol, mixed higher carbon number alcohols, dimethyl ether, Fischer-Tropsch liquids, and/or any combination of these products.

19 Claims, 5 Drawing Sheets

Distribution of World's Gas Fields by Size

Fig.2B  Source: Energy Information Administration, Office of Oil and Gas, Reserves and Production Division (Dallas, TX)

TRACKING FEEDSTOCK PRODUCTION WITH MICRO SCALE GAS-TO-LIQUID UNITS

FEDERALLY SPONSORED RESEARCH

Not applicable.

REFERENCE TO MICROFICHE APPENDIX

Not applicable.

FIELD OF THE INVENTION

This invention relates to small scale stranded natural gas/methane field/source monetization.

BACKGROUND OF THE INVENTION

Small and micro scale processes, including processes utilizing certain portable equipment, are described in detail in U.S. application Ser. No. 12/040,500 filed on Feb. 29, 2008, entitled "Fischer-Tropsch and Oxygenate Synthesis Catalyst Activation/Regeneration in a Micro Scale Process," the disclosure of which is incorporated by reference herein in its entirety.

As used herein the terms "natural gas" and "NG" are used to refer to natural gas, methane or combinations thereof. The terms "natural gas" and "NG" are used to refer to such compositions irrespective of the source. Thus, the terms "natural gas source," "natural gas resource," "natural gas well," "natural gas field," "NG source," "NG resource," "NG field," and "NG well" refer to any source of natural gas or methane including by way of example, natural gas wells, associated gas wells, gas condensate wells, shale gas wells, landfill gas (LFG) sources, coal bed methane (CBM) wells, and gas hydrate deposits.

In conventional land-based Gas-to-Liquids (GTL) processes, the terms "stranded-" or "remote" gas typically have negative implications. First, as suggested by the descriptions, the gas is typically physically removed from potential markets. Second, conventional economic analyses indicate that economies of scale require relatively large plants in order to generate acceptable returns on investment. Although there is some variability, the minimum economically viable size of a conventional Fischer-Tropsch (FT) based GTL plants is typically in the range of 10,000-20,000 barrels per day (bbl/d) hydrocarbon liquid product, or greater (often >50,000 bbl/d). FT GTL plants recently built or currently under construction have capacities of about 34,000 bbl/d (Sasol "Oryx" in Qatar) and about 140,000 bbl/d (Shell "Pearl" in Qatar). A plant having a smaller capacity (e.g., 10,000 bbl/d hydrocarbon liquid product) with an assumed high conversion efficiency of only 8,000,000 BTU per barrel of oil equivalent product, would require at least 80,000,000,000 BTU/day synthesis gas ("syngas") feed. At an assumed gas composition consistent with 1,000 BTU per standard cubic foot ("SCF") of natural gas ("NG") this production rate would require 80,000,000 SCF/day ("SCFD") of feed NG, which is considered a large production requirement. Comparable rates for larger plants would be almost 300 million SCFD to produce about 34,000 bbl/d liquid product and about 1.1 billion SCFD to produce about 140,000 bbl/d hydrocarbon liquid product.

Similarly, in order to achieve acceptable returns on investment, large chemical processing plants such as those employed for GTL are generally expected to operate for at least 20, and more commonly, 30 years. Assuming a 20 year plant life and 350 operation days per year, the total feedstock requirements for a 10,000 bbl/d hydrocarbon liquid product plant would be in the range of 560 billion cubic feet (0.56 trillion cubic feet, or "TCF"). For a 20,000 bbl/d plant with a 30 year life, the total feed would increase to about 1.7 TCF. Plants having the capacity of the Sasol "Oryx" plant or the Shell "Pearl" plant would require about 3 and over 11 TCF, respectively, assuming 30 year plant lives.

Methanol synthesis is much more common today than Fischer-Tropsch synthesis. Historically (generally up to about 1990) methanol synthesis plant sizes have been rather smaller, in the range of 10,000 to 1,000,000 metric tons of product per year. This corresponds to approximately 230 to 23,000 bbl/d methanol product. The majority of methanol synthesis plants based on NG feedstocks constructed since about 1990 have been larger, in the range of 500,000 to 2,000,000 metric tons/year (11,000 to 45,000 bbl/d of methanol), again for economic reasons identical to those for FT based plants. Unlike conventional crude oil or Fischer-Tropsch based hydrocarbon products, methanol contains substantial oxygen (approximately 50% by weight); therefore its energy density is almost a factor of 2 lower and about twice as many barrels of methanol (as compared to FT hydrocarbons) can be produced from a given quantity of NG feed. Thus a 45,000 bbl/d methanol synthesis GTL plant is more or less comparable in feedstock requirements to a 20,000 bbl/d FT based GTL plant. In the following GTL plant volumetric production rates will be based on hydrocarbon products and energy densities, it being understood that for methanol synthesis based processes the volumetric production rates will be approximately a factor of 2 larger.

Table 1 and FIG. 1 show representative distributions of known natural gas fields, including fields considered remote, stranded, not remote and not stranded (Table 1 includes only fields outside of North America as of 1992 (Ivanhoe, L. F., Leckie, G. C., "Global Oil, Gas Fields, Sizes Tallied, Analyzed", Oil and Gas Journal, Feb. 16, 1993)). As shown in Table 1, there are only about 100-200 fields with reserves consistent with the larger conventional land-based GTL plants. The number of fields with sufficient reserves that are stranded and/or remote, such that the gas cost would be low enough to justify a GTL plant, is significantly smaller. Most of the largest stranded fields are prime candidates for gas monetization by production of liquefied natural gas (LNG), a more technologically developed process than GTL; for this reason LNG is generally perceived as being significantly less risky than GTL and is, therefore, much more common commercially.

TABLE 1

| Natural Gas Field Size (TCF) | Number |
| --- | --- |
| Between 50 and 500 | 15 |
| Between 5 and 50 | 71 |
| Between 1 and 5 | 234 |
| Between .5 and 1 | 269 |
| Between .25 and .5 | 276 |
| Between .1 and .25 | 475 |
| Between .01 and .1 | 1,195 |
| Less than .01 | 1,913 |

Table 1 and FIG. 1 also show that there are a much larger number of smaller fields, which are too small to accommodate the natural gas feed rates economically required by very large, long life land-based GTL or LNG facilities.

There have been a number of proposals for mobile, marine based GTL plants, typically at somewhat smaller sizes—1, 000-20,000 bbl/d hydrocarbon liquid product—mounted on platforms, barges, and/or floating production, storage and offloading/offtake ("FPSO"s) ships. Because such facilities would be movable, smaller natural gas fields could be converted to liquid products with these units. For a 1,000 bbl/d unit hydrocarbon liquid product production rate, a feed rate of at least 8-10 million SCFD (MMSCFD) would be required. To supply such a production unit for five (5) years, a natural gas field would have to supply 14 billion standard cubic feet (or 0.014 TCF) natural gas. Such units could greatly expand the monetization of stranded marine/offshore natural gas, but would not address the problem of small onshore stranded and/or remote gas resources. In addition, offshore environments can be relatively challenging to conventional refinery/chemical plant processes due to considerations such as wave motions, limited surface/plot areas, and limitations on maximum vessel height and weight. Currently, such proposed processes have not been successfully commercially developed.

In order to be fully movable and/or transportable on shore, a GTL plant would need to be smaller than even 1,000 bbl/d hydrocarbon liquid product capacity. Actual size would be highly dependent on the specific technologies employed and their packaging, but the maximum size is almost certainly smaller than 1000 bbl/d, and probably as small as 200 bbl/d hydrocarbon liquid product, for units that would be transportable by conventional trucking methods. GTL plants at this scale have been constructed and operated by a number of companies, including ExxonMobil, ConocoPhillips, Sasol, BP, and Syntroleum, and have generally been referred to as Process Development, or Demonstration, Units ("PDU"s). Despite their small size (between 50 and 400 bbl/day hydrocarbon liquid product), such constructed units have all been: (1) too large to be readily transportable; and (2) uneconomic except for R&D purposes. Specifically, capital costs for these "PDU"s have been in the 20 to 50 million dollar range, or higher, with the net operating costs in the range of millions to tens of millions of dollars per year. In general, such PDUs were operated for a few years to provide process scale-up data, and then shut-down or mothballed at least as soon as possible once these programs were completed.

An additional issue in economically monetizing small natural gas supplies—aside from low total reserves (i.e., leading to short production life) and relatively low flow rate (i.e., small capacity plants)—is the tendency of the maximum NG production rate of gas sources, of any total size, to change over time. In fact the gas production rate often changes significantly over the life of the resource or field. FIGS. 2-4 show typical natural gas production rates versus time for traditional gas field wells, landfill gas (LFG) sources, and coal bed methane (CBM) wells, respectively.

FIGS. 2-4 indicate that the NG production rate from any of these sources is almost never constant, and typically declines, often significantly and rapidly. In addition, NG production generally increases significantly early in the life of a field or landfill, often over a period of months or even years, and then may increase again during subsequent source treatments, such as well fracturing, refracturing, or other workover or stimulation treatments, later in the life of the well. In general, the rate of NG production decline is larger for smaller fields, so that low production rate wells with short productive time spans typically go hand in hand.

Generally, large processing plants are built in parallel units, commonly referred to as "trains." The trains are typically sized either by feedstock availability, total cost, or maximum size of particular parts of the process equipment. For GTL plants all three limitations are possible. Natural gas field size or stable production rate, and total capital cost exposure or risk are the most common limitations of the first two types. Either synthesis gas generation equipment (typically reactors) and/or maximum oxygen plant train size are the common limitations of the third type. For large plants additional trains may be added, but, historically, are almost never removed, while capacity is expected to be constant or increasing with time, although economic considerations (e.g. monetary losses) may result in the shutting down ("mothballing") of one or more (or all) trains. The decrease in NG production which normally occurs in each and every well is countered by bringing additional production wells into service on a more or less continuous basis, such that total field/resource NG production is more or less constant or even increasing to meet demand until the resource/field itself is depleted.

When considering monetizing small gas resources, the typical decline in well NG production is more problematic because the micro-GTL plants are sized to handle the production from only a small number of wells, in the range of between about 1 and about 20 wells. Constant NG feedstock production from the well(s) is therefore unlikely. It may be possible to limit the NG production from a single well to match the capacity of an installed micro-GTL unit. Such a scenario, however, is less attractive for the resource owner who would prefer to operate at the highest possible production rate consistent with reservoir integrity to maximize cash flow. U.S. Pat. No. 7,067,561 describes a multi-train GTL plant whereby the overall capacity can be adjusted to match available feed by closing off trains. While the process described in U.S. Pat. No. 7,067,561 would allow maximum NG production and monetization as production naturally declines, the overall economics of the project would suffer, as the entire GTL unit would be underutilized for a significant fraction of the life of the field. In practice, some limitation on field production rate—typically in the range of 50% of maximum NG production rate—may be required in order to provide for relatively constant gas flow, but production should be maximized consistent with this general requirement.

When a new NG resource is suspected or discovered, tests to measure the capacity of the resource prior to making the decision to install relatively costly gas gathering, treatment, and transportation (pipeline or other) facilities are generally conducted. Otherwise, it may later be discovered that the NG resource was too small to justify the investment. For NG fields such testing typically entails drilling a number of wells around the suspected extent of the field and then producing NG for as long as several years to measure the long term production performance (i.e. "decline curves") of each well. In the absence of gathering, treatment, and transportation infrastructure, gas produced during these tests is usually flared, re-injected, or, less commonly, vented. This is especially common in newly discovered NG sources, where conventional transportation infrastructure, especially pipelines, may be entirely absent. The lost value of this production test NG can be measured in the millions of dollars. Should these tests indicate sufficient total field size and production rates to justify the investment, NG gathering, treatment, and transportation (e.g. pipeline) facilities may then be installed. Similarly, even in the presence of an existing gas transportation pipeline, for example, connection charges to such existing facilities may be so high as to require multiple well decline curve tests/measurements to justify the connection expense. Thus, even relatively large NG resources located close to substantial markets (in other words, gas that would not normally be considered stranded) may, in fact, be stranded for a period of time, often measured in years, during initial field development and well testing.

It would be extremely beneficial if a low capital and operating cost, fully transportable and/or movable technology platform existed that could economically monetize small stranded NG fields or other sources (i.e. landfill gas) on shore.

SUMMARY OF THE INVENTION

Embodiments of the invention provide methods of tracking production from a source of natural gas that includes the steps of: (i) providing one or more micro-scale GTL units; (ii) feeding natural gas from the natural gas source to the one or more micro-scale GTL units; and (iii) adjusting the number of micro-scale GTL units employed to track or match the production from the source. In some aspects of the invention, the micro-scale GTL units have a gas feed rate ranging from about 200 to about 1,000 MSCFD. In yet other embodiments, the micro-scale GTL units have a gas feed rate of about 500 MSCFD. In a preferred embodiment, the source is expected to produce from about 1 to about 10 years.

In some embodiments of the invention, the micro-scale GTL unit include both syngas production units and liquid hydrocarbon product synthesis units. In some aspects, the liquid product synthesis units use the syngas produced in the syngas production unit to produce methanol, mixed higher carbon number alcohols, dimethyl ether, Fischer-Tropsch liquids, and/or any combination of these products.

In yet other embodiments, the methods further include the step of upgrading the liquid hydrocarbon product. In some aspects, the liquid hydrocarbon product is methanol, dimethyl ether or a combination thereof. In yet other embodiments, the methanol and/or dimethyl ether is converted to gasoline in the step of upgrading.

In certain aspects of the inventive methods, the step of liquid product upgrading includes hydrocracking and/or hydroisomerization of FT liquids to produce synthetic diesel and/or high quality lubricant products.

In some embodiments of the inventive methods, the method further includes the step of providing a mobile activation/regeneration unit. In some embodiments of the inventive methods, the method further includes the step of providing a hydrogenative prereformer. In some embodiments of the inventive methods, the method further includes the step of providing a mobile start-up unit.

In some embodiments of the inventive methods, the method further includes the step of feeding NG to the one or more micro-scale GTL units involves providing NG from a single NG source. In other embodiments, such step includes providing NG to the one or more micro-scale GTL units from a plurality of NG sources. In some aspects, the single NG source is a natural gas well, an associated gas well, a gas condensate well, a shale gas well, a landfill gas (LFG) source, a coal bed methane (CBM) well, or a gas hydrate deposit. In some aspects, the plurality of NG sources includes two or more sources selected from the group of natural gas wells, associated gas wells, shale gas wells, landfill gas (LFG) sources, coal bed methane (CBM) wells, and gas hydrate deposits.

In other embodiments, the method further includes the step of transporting the micro-scale GTL liquid products in an existing, conventional liquid (i.e. crude oil) pipeline. This is especially important in the case of associated gas wells, where currently the liquid products may be produced while the associated gas is re-injected, flared, or—less commonly—vented. Some significant deposits of discovered oil are not currently in production because of a lack of acceptable means of associated gas utilization, for example when gas re-injection, flaring, and/or venting are legally prohibited or otherwise uneconomic.

In yet other embodiments, the method further includes the step of preparing the NG source location before the step of providing and utilizing one or more micro-scale GTL units. In yet other aspects, the step of preparing the NG source site minimizes infrastructure, environmental, construction and architectural changes to the NG source site in order to minimize remediation work at the termination of operations.

In some embodiments, the plurality of NG sources feeding one or more proximate micro-scale GTL units are physically linked together and/or located in a restricted geographical area. The definition of a restricted geographical area is somewhat dependent on local conditions, but in general would rarely be larger than perhaps 5-10 miles in diameter because of the costs involved in gathering multiple sources to a single production facility. Sources spaced at larger distances it will, in general, be more economically monetized by dispersing the one or more micro-scale GTL units closer to individual or smaller groups of NG sources. In yet other aspects, the plurality of NG sources consists of between 2 and 20 NG sources.

BRIEF DESCRIPTION OF THE DRAWINGS

FIG. 2a-2c illustrate typical natural gas well production curves.

DETAILED DESCRIPTION OF THE INVENTION

Figure 1:
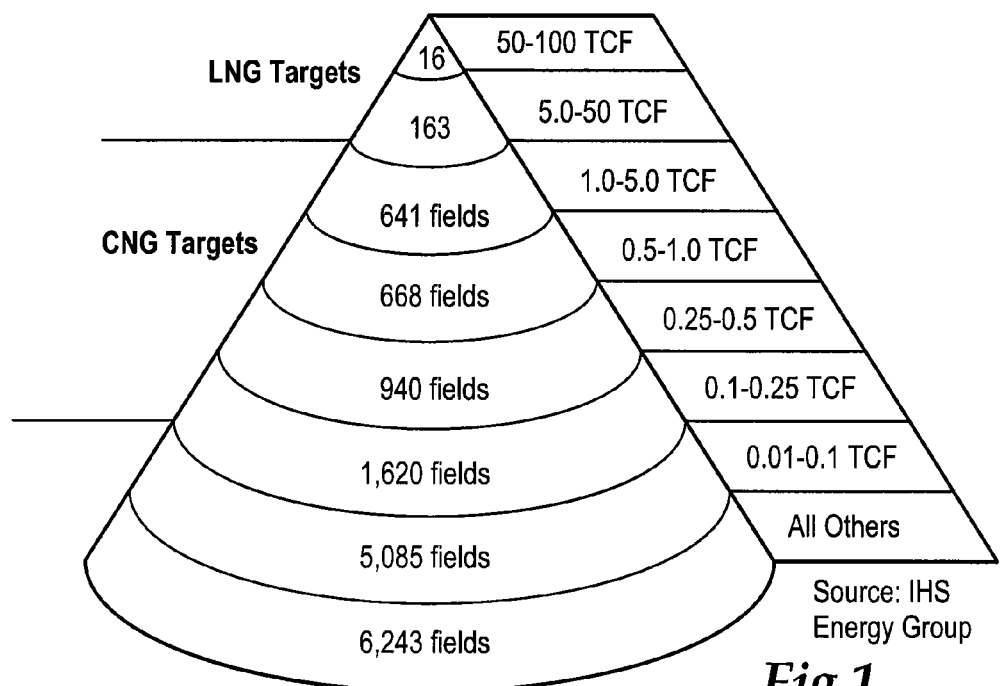
FIG. 1 is a schematic illustrating natural gas field size distribution.
Figure 2A:
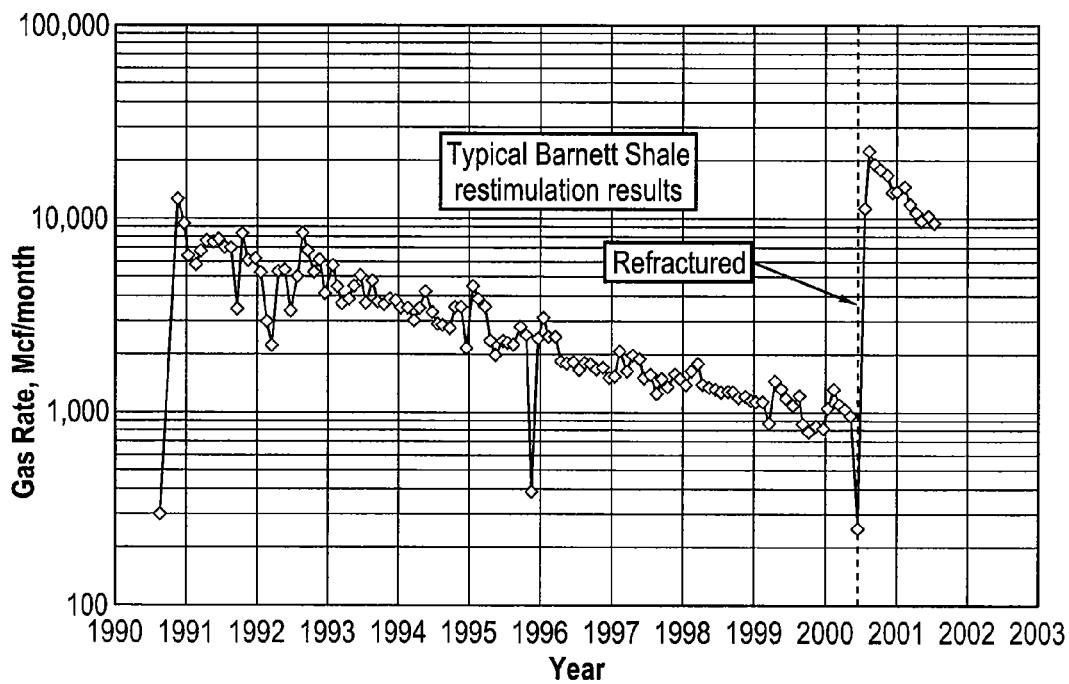
Figure 2C:
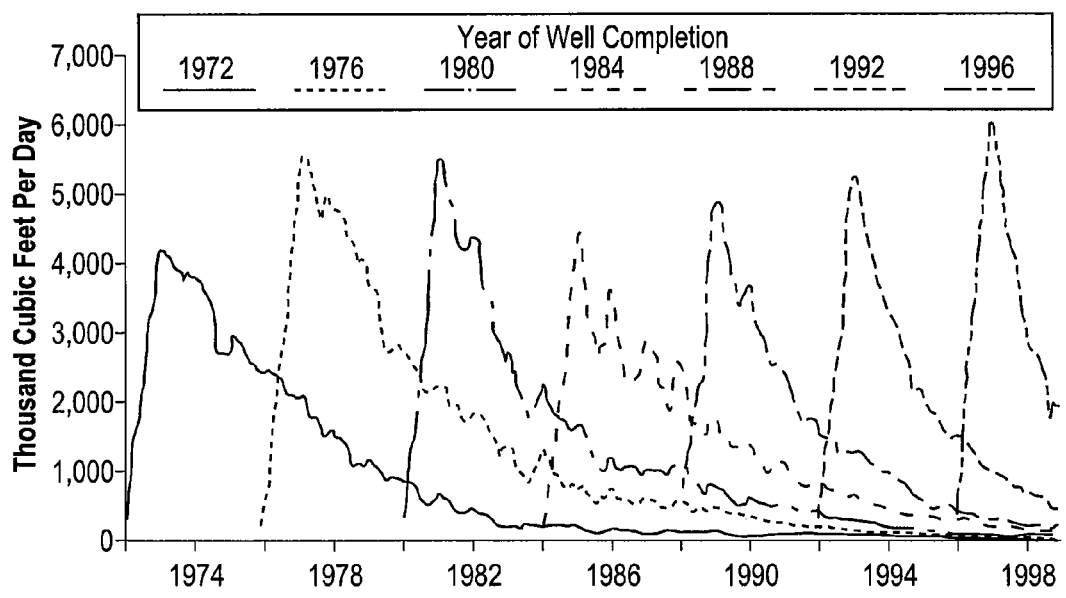
Figure 2C:
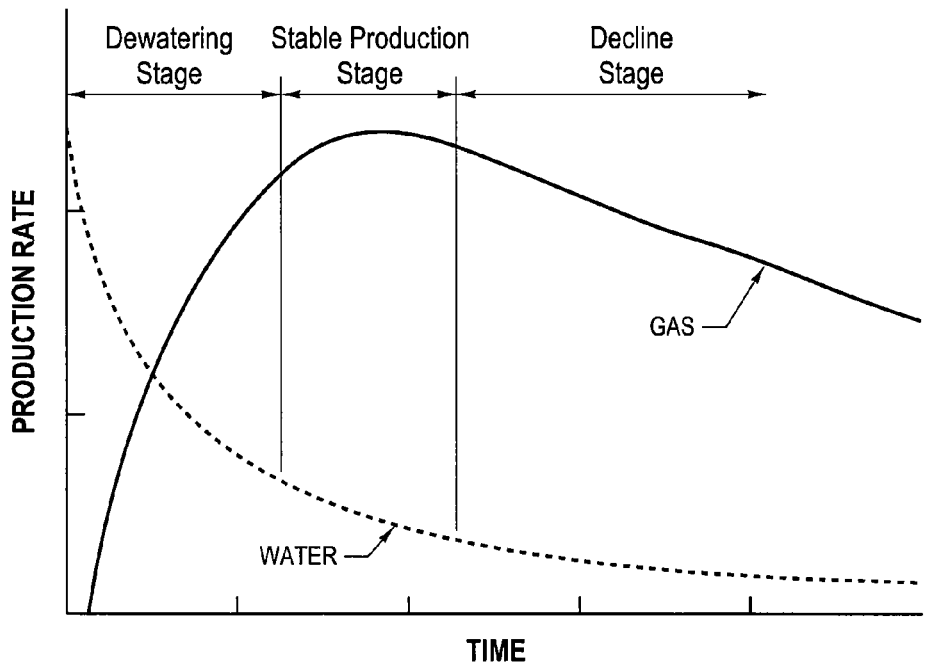
Figure 3A:
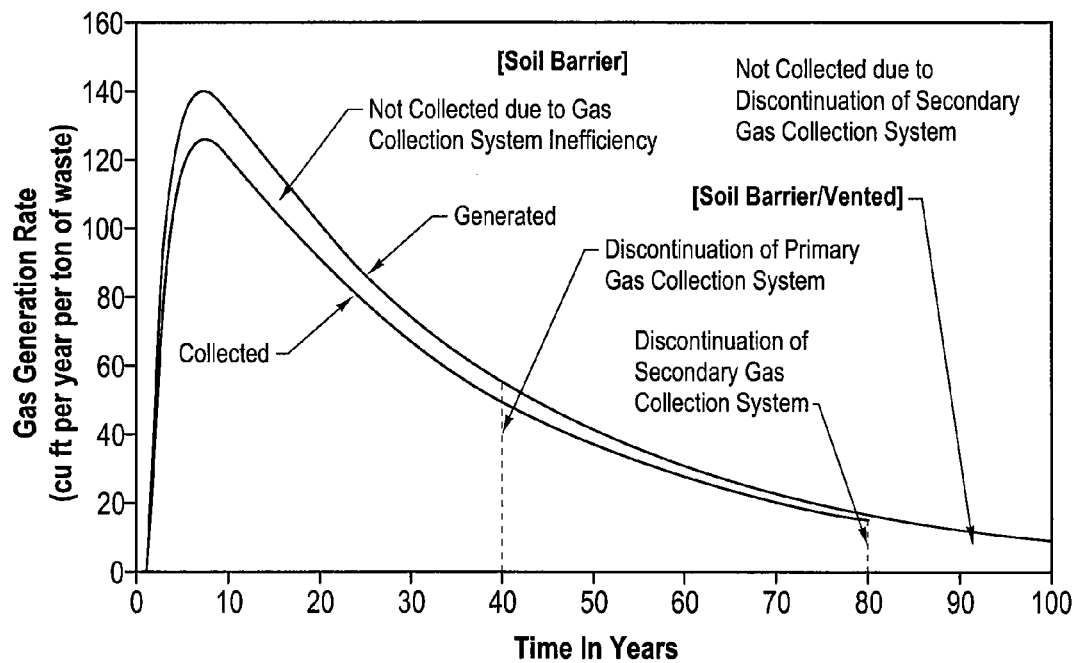
FIG. 3a-3d illustrates typical landfill gas production curves and compositions.
Figure 3B:
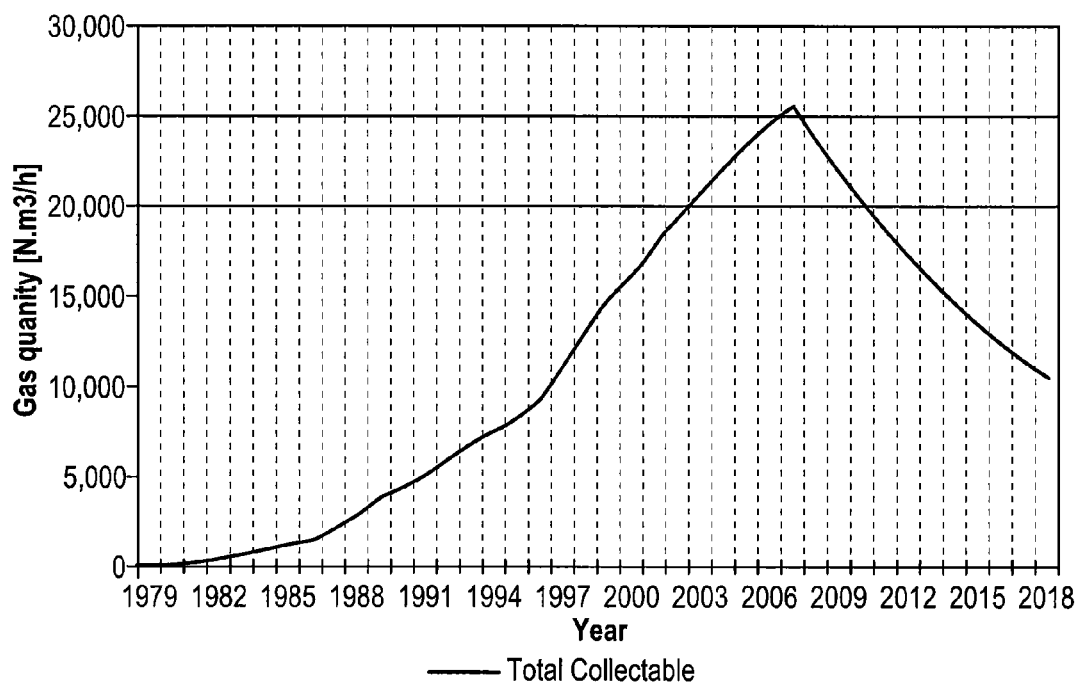
Figure 3C:
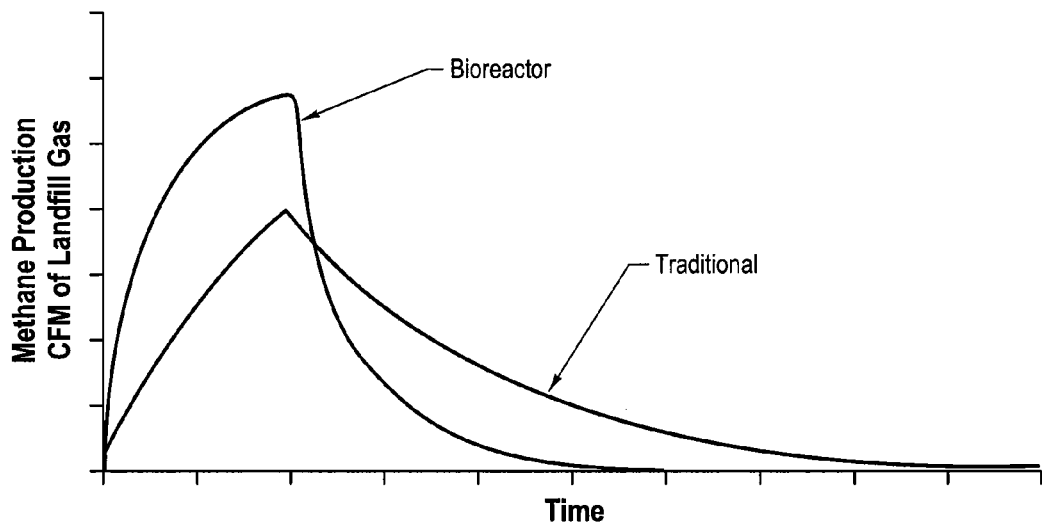
Figure 3D:
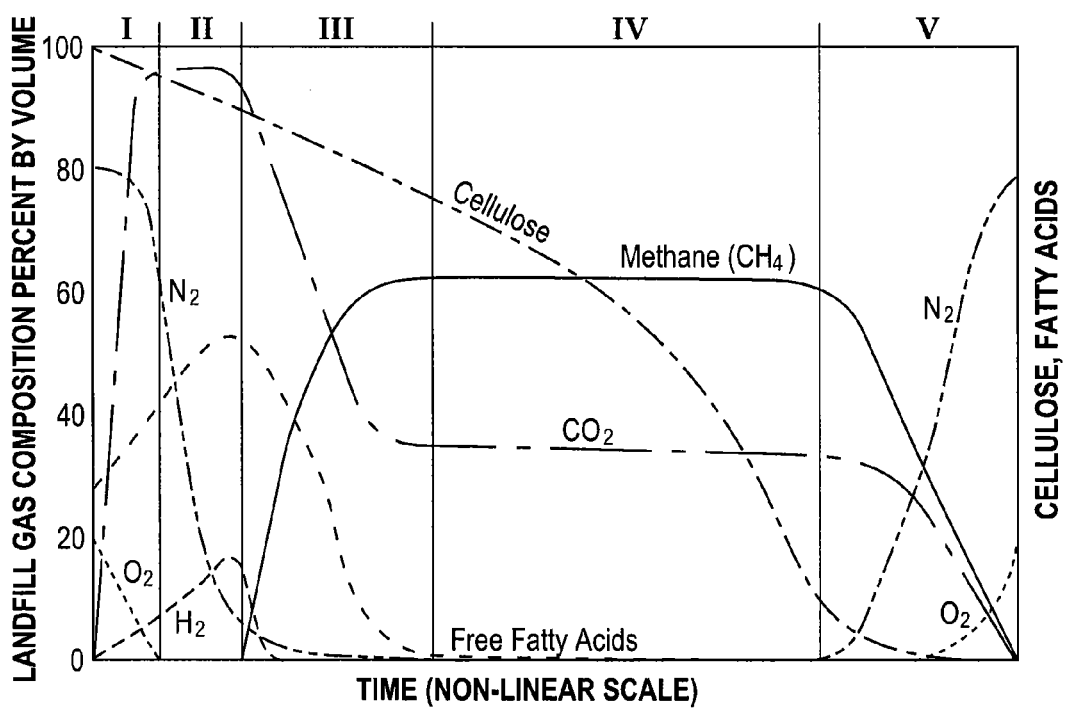
Figure 4:
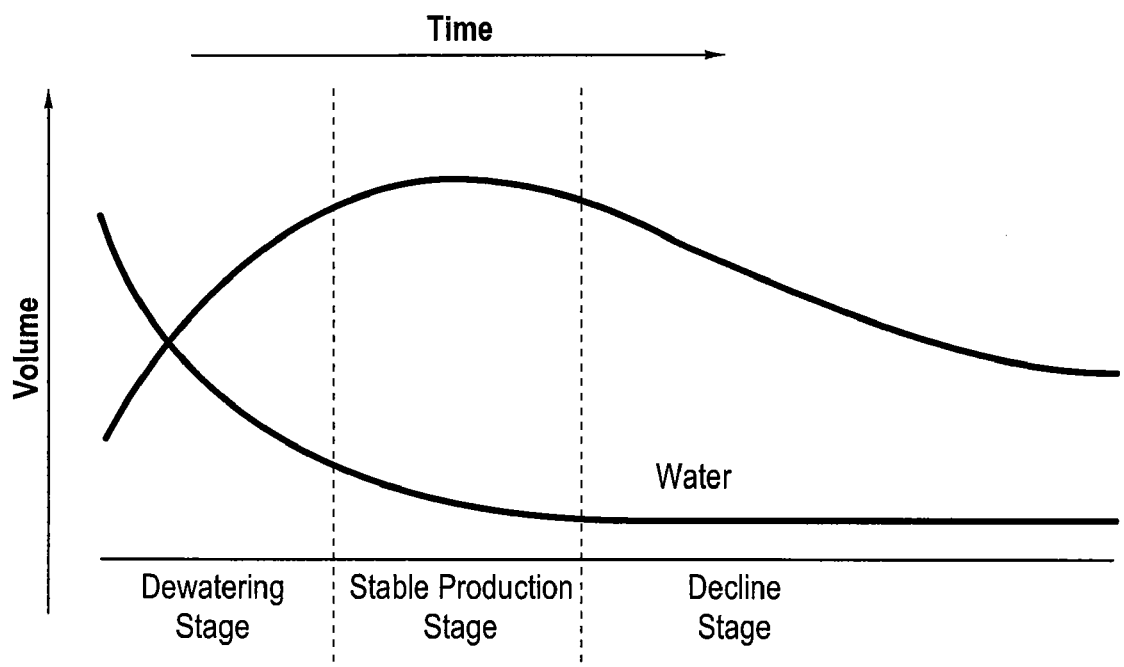
FIG. 4 illustrates a typical coal bed methane (CBM) production curve.

In one embodiment of the invention, micro-scale FT and oxygenate synthesis plants are contemplated for monetizing small gas fields. In some embodiments, such plant capacities may range from about of 200 to about 1000 thousand SCFD (MSCFD) NG feed rates, which are equivalent to from about 20 to about 100 bbl/d hydrocarbon liquids production capacity. In other embodiments, such plant capacities may range from about 1 to about 10 MMSCFD NG feed rates, which are equivalent to from about 70 to about 1,000 bbl/d hydrocarbon liquids production capacity. Without being bound by any theory, there is no reason that technically viable units could not be smaller still, in the range of about 100 to about 200 MSCFD NG feed rates (about 10-20 bbl/d hydrocarbon liquid product); minimum size is strictly a function of economic viability.

In some embodiments, one or more micro-scale GTL trains may be used. In some embodiments, the one or more micro-scale GTL trains may be identical or may combine various "standard" designs. In some embodiments, there are between 3 to 5 standard designs. The trains may be in the size range of what has previously been considered to be Process Development/Demonstration Unit (PDU)-scale, nominally in the range of about 20-200 bbl/d liquid hydrocarbon (i.e., Fischer-Tropsch ("FT")) products.

There are a number of constraints on the economic viability of plants at the micro-scale level. A recently constructed commercial conventional FT based GTL plant (Sasol "Oryx", in Qatar) cost in the range of about $950 million for approximately 34,000 bbl/d FT liquid products, or about $28,000 per bbl/d hydrocarbon liquid product capacity. More recently, engineering, procurement, and construction ("EPC") costs have increased such that currently forecasted GTL capital costs for plants to be constructed in the near future are in the range of $50,000 per bbl/d hydrocarbon liquid product for similarly sized conventional plants. As plant size is increased from $S_1$ to $S_2$, the ratio of costs increases nonlinearly, i.e., by some power other than 1. For example, consider two conventional facilities having different capacities, $S_1$ and $S_2$. The cost of the second facility ($C_2$) may be determined using a "scale factor" and the cost of the first facility ($C_1$), according to the formula, $C_2 = C_1 * (S_2/S_1)^n$, where "n" is the scale factor. For n<1, costs rise at less than the ratio of plant size/capacity, so unit cost decreases yielding what is referred to as "economies of scale". At a conventional plant scale factor of 0.6 these cost projections suggest that a 50-100 bbl/d hydrocarbon liquid product train would cost in the range of $19-29 million (at $28,000 per bbl/d hydrocarbon liquid product for the larger, conventional unit) to $34-51 million (at $50,000 per bbl/d hydrocarbon liquid product). Using the more recent specific capital cost prediction of $50,000 per bbl/d hydrocarbon liquid product capacity, and assuming a $50/bbl product price, the ratio of plant capital cost to total plant yearly revenue would vary from about 3.0 for a 34,000 bbl/d hydrocarbon liquid product plant to 31 for a 100 bbl/d hydrocarbon liquid product plant and 40 for a 50 bbl/d hydrocarbon liquid product plant. Even with zero costs for operating and maintenance (i.e., all revenue is profit) the time to pay back initial investment on such micro-scale plants is longer than the typical plant lifespan of 20-30 years. With the same $50/bbl product value assumption, actual total yearly revenues for these micro-scale 50-100 bbl/d hydrocarbon liquid product plants would range from about $850,000 to $1,600,000.

The large (14,000 to 45,000 bbl/d) methanol based GTL plants that have recently been constructed (e.g. completed in 2005-2006) have ranged in specific cost from about $90,000 to $180,000 per metric ton per day methanol capacity. These plants were largely completed before the recent large escalation in engineering, procurement and construction (EPC) costs occurred. Taking $100,000 per metric ton/day at 20,000 bbl/d methanol capacity, a normal scale factor of 0.6 would predict a specific cost of $10-15 million for a micro-scale methanol GTL plant producing 100-200 bbl/d methanol. The most recent small methanol plant that has been constructed (a Metaprocess plant for Novatec in Russia, 2007) reportedly cost about $10 million for approximately 250 bbl/d methanol capacity, consistent with a scale factor of about 0.7. Assuming a methanol product value of $1.00 per gallon ($42/bbl) actual total yearly revenues for these micro-scale 100-200 bbl/d methanol plants would range from about $1,500,000 to $3,000,000, while that from a $280 million capital 22,000 bbl/d conventional plant would be about $320 million. The ratio of plant capital cost divided by yearly revenue would therefore range from 0.875 for a large plant to 5-6 for a micro-scale plant, or by about a factor of 5.5 to 7.0. This is somewhat better than the factor of 10 calculated for FT based plants above, although it does not include more recent EPC cost increases, but still suggests it would be difficult to achieve any return on investment (pay back the initial plant capital costs), even with very low or zero operating costs.

Thus, to achieve economic feasibility, plant capital investment costs for such micro-scale GTL plants must be significantly lower than the values predicted from large plant configurations, approaching a factor of 5-10 (or more) times lower, and annual total operating and maintenance costs should be much lower than the relatively small total annual revenue stream.

To achieve these economic targets, certain changes to conventional plants may be necessary. Capital costs may be minimized by minimizing the number of unit operations. The number of vessels, instruments, and rotating equipment may also be minimized. Such micro-scale GTL plants are preferably not individually designed and engineered, but rather are engineered as a small number of standard designs that may be mass produced. The trains may be shop fabricated, modular, and fit within normal truck bed shipping size constraints, e.g., 8 ft.×10 ft.×40 ft. and less than about 20 tons total weight each. Alternatively, a single processing unit may be shop fabricated in more than one module, depending on targeted capacity and/or specific technology requirements. For the very exothermic syngas generation and FT/oxygenate synthesis processes, heat exchanger size may be minimized, utilizing, for example, advanced finned tube designs. In some instances, required utilities, typically electrical power and boiler feed water/steam systems, may be applied as widely as possible, minimizing the number of different utilities included in the plant package.

In some embodiments of the invention, the syngas production includes use of a hydrogenative pre-reformer. Pre-reformers for use in syngas generation are described in detail in U.S. application Ser. No. 12/061,355, filed on Apr. 2, 2008, entitled "Hydrogenating Pre-Reformer in Synthesis Gas Production Processes," the disclosure of which is incorporated in its entirety herein by reference.

Operating costs may also be minimized. In some instances, the micro-scale GTL plants may be highly, if not completely, automated. In other instances, the automated control systems may be capable of remote monitoring and control. In some instances, feed costs may be minimized, by use, for example, of stranded and/or non-pipeline standard (sub-quality) natural gas, most types of coal, and/or waste-stream biomass (including but not limited to, poultry litter, sawmill wastes, agricultural residues, (Kraft paper process) black liquor, municipal solid waste). These latter, non-NG feedstock sources, will typically require alternative synthesis gas manufacturing processes, such as gasification, a large number of which are known in the art.

Maintenance frequency and costs may also be minimized by judicious equipment selection and process design and layout. In some instances, connections are welded (to avoid leaks associated with gaskets and fittings) except where maintenance constraints dictate flanges or other non-welded connections. Small-scale materials of construction considerations may result in "alloying up" to FeCr (or higher) alloys, compared to the more common large plant carbon steels.

It will be apparent to one of ordinary skill in the art that the foregoing embodiments of the invention may be practiced in connection with processes that produce: (1) only Fischer-Tropsch products; (2) only oxygenate products, including not only methanol and/or dimethyl ether (DME) but also $C_{2+}$ alcohols, including for example, ethanol (EtOH), propanol, butanol, pentanol, etc., as well as tert-amyl alcohol (TAA), and tert-butyl alcohol (TBA); (3) a combination of Fischer-Tropsch and oxygenate products, (4) particularly Fischer-Tropsch products and methanol, (5) any type of oxidative or non-oxidative (direct) methane coupling—typically to methanol, mixtures of ethylene (and/or higher olefins)—which can be polymerized to gasoline or diesel range products—and ethane (and/or higher paraffins)—which can be dehydrogenated to olefins and then polymerized—and/or aromatics; (6) methane pyrolysis to acetylene followed by hydrogenation to ethylene and polymerization of the ethylene product (See, e.g., U.S. Pat. Nos. 6,130,260; 6,323,24; 6,433, 235; 6,602,920; 7,045,670; 7,119,240; 7,183,451; and 7,208, 647, the disclosures of which are incorporated herein in their entirety), and (7) processes based on bromine—(See, e.g., U.S. Pat. Nos. 7,348,464; 7,244,867; 7,161,050; 7,148,390; 7,019,182; 6,713,655; 6,525,230; 6,486,368; 6,472,572; 6,465,699; 6,465,696; 6,462,243; and 6,403,840, the disclosures of which are incorporated herein in their entirety), chlorine—(See, e.g., U.S. Pat. Nos. 4,199,533; 4,467,127; and 4,513,092, the disclosures of which are incorporated herein in their entirety), and/or sulfur—(See, e.g., U.S. Pat. Nos. 7,282,603 and 6,380,444, the disclosures of which are incorporated herein in their entirety) containing intermediates.

Methods of direct methane coupling are disclosed in U.S. Pat. Nos. 7,291,321; 7,250,543; 7,176,342; 7,033,551; 7,022,888; 6,924,401; 6,821,500; 6,596,912; 6,576,803; 6,552,243; 6,518,476; 6,500,313; RE37,853; 6,414,195; 6,403,523; 6,380,444; 6,375,832; 6,326,407; 6,294,701; 6,159,432; 6,087,545; 6,028,228; 5,959,170; 5,936,135; 5,935,293; 5,877,387; 5,849,973; 5,817,904; 5,763,722; 5,750,821; 5,749,937; 5,736,107; 5,712,217; RE35,633; RE35,632; 5,670,442; 5,625,107; 5,599,510; 5,585,515; 5,527,978; 5,430,219; 5,414,157; 5,406,017; 5,345,011; 5,345,010; 5,336,825; 5,328,575; 5,321,188; 5,321,187; 5,321,185; 5,316,995; 5,312,795; 5,306,683; 5,276,237; 5,260,497; 5,254,778; 5,246,550; 5,245,124; 5,245,109; 5,238,898; 5,223,471; 5,220,080; 5,214,226; 5,212,139; 5,204,308; 5,198,596; 5,196,634; 5,177,294; 5,157,189; 5,157,188; 5,146,027; 5,132,482; 5,132,481; 5,130,286; 5,118,898; 5,118,654; 5,113,032; 5,105,053; 5,105,046; 5,105,044; 5,095,161; 5,093,542; 5,082,816; 5,081,324; 5,077,446; 5,073,657; 5,073,656; 5,071,815; 5,068,486; 5,068,215; 5,066,629; 5,061,670; 5,053,578; 5,051,390; 5,041,405; 5,028,577; 5,026,947; 5,026,945; 5,024,984; 5,015,799; 5,015,461; 5,012,028; 5,004,856; 4,997,802; 4,996,382; 4,992,409; 4,988,660; 4,982,041; 4,968,655; 4,962,261; 4,952,547; 4,939,312; 4,939,311; 4,939,310; 4,929,797; 4,929,787; 4,921,685; 4,918,257; 4,918,249; 4,914,252; 4,886,931; 4,849,571; 4,827,071; 4,822,944; 4,814,539; 4,808,563; 4,801,762; 4,795,849; 4,795,848; 4,795,842; 4,794,100; 4,791,079; 4,788,372; 4,783,572; 4,769,507; 4,754,095; 4,754,094; 4,754,093; 4,754,091; 4,751,336; 4,751,055; 4,743,575; 4,734,537; 4,728,636; 4,727,212; 4,727,211; 4,727,207; 4,727,205; 4,721,828; 4,704,496; 4,704,493; 4,704,488; 4,704,487; 4,695,668; 4,678,862; 4,672,144; 4,670,619; 4,665,261; 4,665,260; 4,665,259; 4,658,077; 4,658,076; 4,654,460; 4,634,800; 4,620,057; 4,613,718; 4,593,139; 4,568,785; 4,560,821; 4,554,395; 4,547,611; 4,547,608; 4,544,787; 4,544,786; 4,544,785; 4,544,784; 4,523,050; 4,523,049; 4,517,398; 4,499,324; 4,499,323; 4,499,322; 4,495,374; 4,489,215; 4,465,893; 4,450,310; 4,444,984; 4,443,649; 4,443,648; 4,443,647; 4,443,646; 4,443,645; 4,443,644, the disclosures of which are incorporated herein in their entirety.

As described above, a small number of different unit designs may be contemplated before engineering and design costs become uneconomical. In general, different designs may be based on different technology and/or product platforms (e.g., methanol, dimethyl ether, and/or Fischer-Tropsch liquids), although a small number of otherwise identical units of different size/capacity could also be effective. In either case, it is unlikely that either a single or a small number of different sized (i.e. different capacity) units could be optimally applied to a large fraction of the small, stranded and/or remote NG fields available for monetization with these technologies. As shown above, for a larger chosen capacity there are a smaller number of available, appropriately sized fields, and the larger fields are less likely to be stranded, as the larger reserves and higher production rates more easily justify construction of an NG gathering and transportation (e.g., pipeline) system.

There are some constraints on potential unit size. At some minimum size, in the range of about 10 to about 20 bbl/d hydrocarbon liquid product, or 50-200,000 SCFD NG feed rates, micro-scale GTL units will be "too small" to be economical. At some maximum size, they will be too large to be readily transportable. As described above, the maximum size is highly dependent on the specific technologies used and their packaging. In the case of a complete unit contained in a single standard shipping container sized module (i.e. 8 ft.×10 ft.×40 ft. and less than about 20 tons total weight), the maximum size is likely less than between about 150 and about 200 bbl/d hydrocarbon liquid product, and is probably less than about 100 to about 150 bbl/d (e.g. 200 to about 300 bbl/d methanol). While the single standard shipping container size is an important consideration for ease in transportation, technology specific requirements may require modifications. Synthesis reactor size and/or geometry requirements may, for example, require a second, taller structure, in order to accommodate a reactor height larger than 8-10 feet, that would be shipped as a separate module and connected to the primary module at the NG production site.

Choosing a relatively small and fully transportable, but large enough to be economical, standard plant size, in the range of between about 200 and about 1,000 MSCFD NG feed rate, and more preferably about 500 MSCFD, yields the best overall solution to the problems of monetizing small, stranded gas sources described above. Such micro-scale GTL units are small enough to be readily transportable, such that a typically short resource life (e.g. <<20-30 years) does not irreparably debit the project economics; once an NG field/resource is depleted the unit can be relocated to another NG source. If the NG production is significantly greater than the capacity of a single micro-scale GTL unit (~500 MSCFD or greater), additional micro-scale GTL units may be employed in parallel. In theory, there is no limit to the number of micro-scale GTL units that could be employed at the same NG source, although something in the range of between about 15 and about 20 units is probably a practical limit due to the fact that larger NG sources are increasingly less likely to be stranded. As NG production decreases, units can be removed and relocated to other NG sources so that equipment underutilization is minimized or eliminated. However, if NG production later increases significantly, for example after a well stimulation, or other, treatment, additional micro-scale GTL units may be supplied and connected to effectively and efficiently monetize the additional NG feedstock.

The liquid production rate for such a unit can vary, depending strongly on feed gas rate—which may be decreased by up to 50% (or more) depending on well or field production—as well as gas composition, especially the concentrations of inert gases such as helium or nitrogen (which decrease production), $CO_2$ (which can increase production somewhat), and higher hydrocarbons such as ethane, propane, butane, etc. (which can increase production markedly).

It is common for low NG production wells, especially those at very low pressures, on artificial lift, and/or relatively late in production life, to produce only intermittently. The resulting highly variable flow rate(s) can be problematic for downstream production and/or conversion equipment, such as compressors and reactors. Under such conditions, it is common to employ intermediate gas storage and/or tankage to provide a buffer to smooth out the flow rate. Alternatively in-fill NG wells may be drilled and added over time and/or multiple NG wells in the area may be tied in to a gathering system to average out the individually varying flows.

Most conventional on shore processing plants are relatively large and expected to operate for at least 20 to 30 years, although in practice many operations continue at a single site for significantly longer periods of time. Site remediation, clean-up, and restoration is therefore not commonly considered prior to construction and operation of the plant. More commonly, site remediation, clean-up, and restoration would only be considered in light of a possible decision to permanently shut the facility down. For micro-scale GTL plants, the NG resource is not expected to produce indefinitely but rather to produce NG about 1 to about 10 years. Therefore, site remediation, clean-up, and restoration should be considered from the onset of production planning, much like the current situation in traditional oil and/or gas production, or, for example, in surface coal mining. Thus traditional permanent infrastructures, especially foundations and/or slabs, would typically be only minimally employed, and large changes and/or modifications to the site avoided. In general, all equipment modules will be self-supporting, not requiring extensive foundations, with drain pans to collect any leakages of liquids, and for safe movement to a drain system for disposal. Storage tanks will be packaged in a manner that will not require foundations at the site, except for compacted ground and liners to contain any spills. Any concrete that was required to be installed during the site preparation and/or construction could be removed when operations are terminated.

Startup procedures and other embodiments of the invention are described in detail in U.S. application Ser. No. 12/104,161 filed on Apr. 16, 2008 entitled "Micro Scale Fischer-Tropsch and Oxygenate Synthesis Process Startup Unit," the disclosure of which is incorporated by reference herein in its entirety.

We claim:

1. A method of utilizing production from a NG source, the method comprising:
   providing one or more micro-scale GTL units each individually having a gas feed rate ranging from about 200 to about 1,000 thousand standard cubic feet per day and production rate from about 20 to about 100 bbl liquid per day, with a combined gas feed rate matching the production from the NG source;
   feeding natural gas from the NG source to the one or more micro-scale GTL units and operating the one or more micro-scale GTL units over a period of time in which the production from the NG source changes; and
   adjusting the number of micro-scale GTL units employed so as to match the combined gas feed rate to changed production from the NG source;
   wherein the micro-scale GTL units are dimensioned to be transportable independently of each other as units within the dimensions of a shipping container sized module of 8 ft×10 ft×40 ft.

2. The method of claim 1, wherein the one or more micro-scale GTL units each have a gas feed rate of about 500 thousand standard cubic feet per day.

3. The method of claim 1, wherein the NG source is expected to produce NG from between about 1 and about 10 years.

4. The method of claim 1, wherein the one or more micro-scale GTL units comprise a synthesis gas generation unit and a liquid hydrocarbon or oxygenate product synthesis unit.

5. The method of claim 4, wherein operating the one or more micro-scale GTL units comprises producing a liquid hydrocarbon or oxygenate product selected from the group of methanol, mixed higher carbon number alcohols, dimethyl ether, Fischer-Tropsch liquids, and any combination thereof.

6. The method of claim 5 wherein the hydrocarbon or oxygenate product is methanol, dimethyl ether or a combination thereof and further comprising converting the methanol, dimethyl ether or combination thereof to synthetic gasoline.

7. The method of claim 5 wherein the hydrocarbon product is a Fischer-Tropsch reaction product and further comprising converting the hydrocarbon product to one or more final products selected from the group of synthetic diesel and lubricants, wherein conversion of the hydrocarbon product includes hydrotreating, hydrocracking, hydroisomerization, or any combination thereof.

8. The method of claim 4 further comprising providing a mobile activation/regeneration unit and using the mobile activation/regeneration unit is configured to activate and/or regenerate one or more catalysts used in the one or more micro-scale GTL units.

9. The method of claim 4 further comprising providing a hydrogenative prereformer.

10. The method of claim 4 further comprising providing a mobile start-up unit and using the mobile start-up unit to start operation of the one or more micro-scale GTL units.

11. The method of claim 1, wherein the one or more micro-scale GTL units is fed by a single NG source.

12. The method of claim 11 wherein the single NG source is a natural gas well, an associated gas well, a gas condensate well, a shale gas well, a landfill gas (LFG) source, a coal bed methane (CBM) well, or a gas hydrate deposit.

13. The method of claim 1, wherein the NG source comprises a plurality of NG sources within a geographical area not more than 10 miles in diameter.

14. The method of claim 13 wherein the plurality of NG sources are selected from the group of natural gas wells, associated gas wells, gas condensate wells, shale gas wells, landfill gas (LFG) sources, coal bed methane (CBM) wells, and gas hydrate deposits.

15. The method of claim 1 further comprising preparing the NG source before providing one or more micro-scale GTL units.

16. The method of claim 13 wherein the plurality of NG sources are physically linked together.

17. The method of claim 13 wherein the plurality of NG sources consists of between 2 and 20 NG sources.

18. The method of claim 1 comprising operating the one or more micro-scale GTL units over a period of time in which the production from the NG source increases and adjusting the number of micro-scale GTL units employed comprises increasing the number of micro-scale GTL units.

19. The method of claim 1 comprising operating the one or more micro-scale GTL units over a period of time in which the production from the NG source decreases and adjusting the number of micro-scale GTL units employed comprises reducing the number of micro-scale GTL units.

* * * * *